10/18/83 OR 4,409,839

United States Patent [19]

Taenzer

[11] 4,409,839

[45] Oct. 18, 1983

[54] ULTRASOUND CAMERA

[75] Inventor: Jon C. Taenzer, Palo Alto, Calif.

[73] Assignee: Siemens AG, Berlin and Munich, Fed. Rep. of Germany

[21] Appl. No.: 281,967

[22] Filed: Jul. 10, 1981

[51] Int. Cl.³ ...................... G01N 29/04; A61B 10/00

[52] U.S. Cl. ........................................ 73/625; 73/642; 128/660

[58] Field of Search ............................... 128/660-661, 128/663; 73/625-626, 642, 644

[56] References Cited

U.S. PATENT DOCUMENTS

| | | | |
|---|---|---|---|
| 3,251,219 | 5/1966 | Hertz et al. | 128/660 X |
| 3,937,066 | 2/1976 | Green et al. | 73/67.5 R |
| 3,971,962 | 7/1976 | Green | 310/8.1 |
| 4,246,791 | 1/1981 | Glenn | 73/620 |
| 4,325,381 | 4/1982 | Glenn | 128/660 |

OTHER PUBLICATIONS

Philip S. Green et al., "A New, High-Performance Ultrasonic Camera", *Acoustical Holography*, vol. 5, 1974, pp. 493-503.

J. R. Suarez et al., "Biomedical Imaging with the SRI Ultrasonic Camera", *Acoustical Holography*, vol. 6, pp. 1-13.

*Primary Examiner*—Kyle L. Howell
*Assistant Examiner*—Francis J. Jaworski
*Attorney, Agent, or Firm*—Karl F. Milde, Jr.

[57] ABSTRACT

The ultrasonic apparatus contains an imaging lens for focusing ultrasound waves, a diverging device for receiving converging ultrasound waves from the lens and for transmitting ultrasound waves such that beams coming from a single object point are focused along a focal line, and an ultrasound detector positioned at the focal line indicating the ultrasound waves. The detector contains a large number of elongated detector elements. In particular, the diverging device comprises an acoustic mirror containing a reflecting surface which has a diverging effect on impinging beams of ultrasound waves. Preferably, the mirror may have a reflecting surface which is formed by a large number of parallel parabolic lines.

10 Claims, 7 Drawing Figures

ULTRASOUND CAMERA

BACKGROUND OF THE INVENTION

1. Field of the Invention

This invention relates generally to an apparatus for generating an image from ultrasonic waves.

2. Description of the Prior Art

Ultrasonic systems of the type herein contemplated are disclosed, for instance, in U.S. Pat. No. 3,967,066, in *Acoustical Holography,* vol. 5, pages 493–503, 1974, and in *Acoustical Holography,* vol 6, pages 1–13.

The U.S. Pat. No. 3,971,962 discloses a linear transducer array for ultrasonic image conversion in an ultrasonic orthographic imaging system (C-scan camera). This prior art transducer array contains a large number of elongated transducer elements. The patent mentions that, from the standpoint of resolution, it would be favorable to design each element of the sampling array to be small and to have equal height and width. In other words, each element should be small in both dimensions. However, there are some problems associated with a small element: the electrical impedance of such an element is very high. This would lead to impedance matching problems in the electric circuits which detect and process the signals derived from the individual elements. This is true, for instance, for the preamplifiers which are connected to each respective element. Poor impedance matching can result in a low signal-to-noise ratio. The high impedance also leads to poor high frequency response due to the shunting effect of the inevitable stray capacitances associated with the element mounting and lead attachments to the elements.

In order to avoid these problems, elongated receiver elements are used in the prior art design disclosed in the above-mentioned patent. Each of the elongated elements corresponds or is equivalent to many small elements which are connected in parallel. A parallel connection of elements has comparatively low impedance. Thus, the impedance matching and high frequency loss problems have been solved. However, simultaneously the resolving power of the array of elements has been reduced in one dimension, that is the dimension of the longitudinal axis of the element. In order to correct this reduction of resolution, the patent suggests employing a cylinder lens which is arranged a short distance in front of the array of elongated elements. The cylinder lens is situated in a position to cause the converging wavefronts from an image-forming lens to collimate in one dimension.

It has turned out that such a cylinder lens may produce undesirable internal reverberations of the ultrasonic waves between the front and back surface of the cylinder lens. Therefore, spurious acoustic waves may be superimposed in the image field received by the elements. The superposition of these waves results in additional patterns superimposed in the true ultrasonic image which is to be displayed. It is highly desirable to avoid the superposition of such patterns.

Application of a cylinder lens may also have another effect. There may occur reflections between the elongated transducer elements and the cylinder lens. The surface of the elements has an impedance which is somewhat different from the impedance of the fluid which is conventionally interposed between the elongated elements and the cylinder lens. Thus, there may occur reflections on the surface of the elements and reflections on the surface of the cylinder lens. Again, this effect will result in undesired patterns in the ultrasonic image.

The cylinder lens itself constitutes an additional complex component, which requires some expeditures. For proper operation, the cylinder lens should be covered by a matching layer. Applying this layer requires some work and is time consuming. Therefore, it is desirable to use elongated low-impedance transducer elements, but to eliminate the otherwise concomitant requirement or necessity of a cylinder lens.

SUMMARY OF THE INVENTION

1. Objects

It is an object of this invention to provide an ultrasonic apparatus which uses elongated low-impedance receiver elements, and in which the use of a cylinder lens is nevertheless avoided.

It is another object of this invention to provide an ultrasonic image generating apparatus in which superimposed patterns due to internal reverberations are avoided.

It is still another object of this invention to provide an ultrasonic orthographic imaging apparatus having elongated transducer elements, in which the converging wavefronts from an image-forming lens are caused to collimate in one dimension without the requirement of an additional cylinder lens.

2. Summary

According to the invention, an ultrasound apparatus is provided which contains a focusing device for focusing ultrasound waves coming from an object under examination, preferably from a patient. The apparatus also contains a diverging device that receives the focussed ultrasound waves. It is the task of this diverging device to transmit waves coming from a single point to a focal line. The ultrasonic apparatus also incorporates an ultrasound detector positioned at the focal line for receiving the focused ultrasound waves. The detector contains a certain number of elongated piezoelectric detector elements, that is, a so-called sensor array.

According to this invention, the diverging device comprises an acoustic mirror. This mirror has a reflecting surface which exerts a diverging effect on an impinging beam of ultrasound waves. The acoustic mirror is preferably positioned between the focusing device and the ultrasound detector. According to a preferred embodiment, the reflecting surface of the acoustic mirror is formed by a large number of parallel parabolic lines which are convex with respect to an impinging ultrasound wave.

In the ultrasonic apparatus, according to the invention, the conventional cylinder lens is avoided. Therefore, reverberations within the cylinder lens, and between the cylinder lens and the detector array, as well as between the main focusing or imaging lens and the cylinder lens, are eliminated. Thus, any image degradations due to such reverberations involving the cylinder lens are avoided.

Due to the lack of the cylinder lens, also another advantage is obtained. Any attenuation (absorption, reflection) of ultrasound intensity which is regularly caused by the conventional cylinder lens is eliminated. Finally, the size of the side lobes in the intensity distribution which prevails on the ultrasound detector is decreased.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 4:
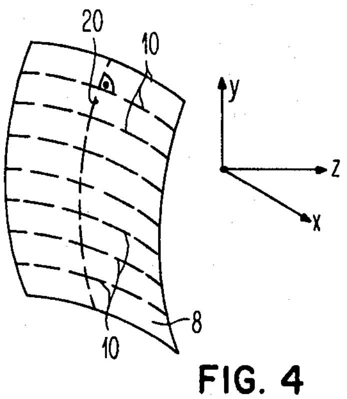
FIG. 4 is a perspective view of a parabolic mirror having a curved section line connecting perpendicularly the individual cross-sectional lines.
Figure 5:
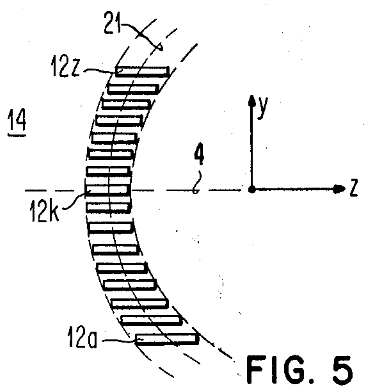
FIG. 5 is a face view of the detector array used in the first embodiment shown in FIG. 1.
Figure 6:
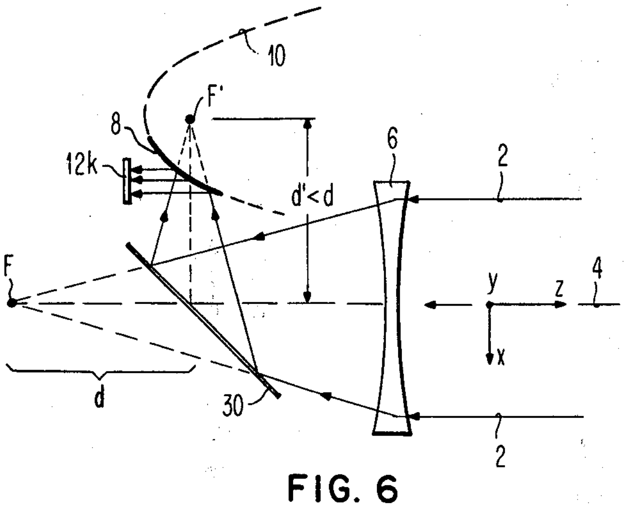
FIG. 6 is a cross-sectional view of the receiving unit of an ultrasonic apparatus according to a second embodiment of this invention, wherein a "plane" mirror and a parabolic mirror are used.
Figure 7:
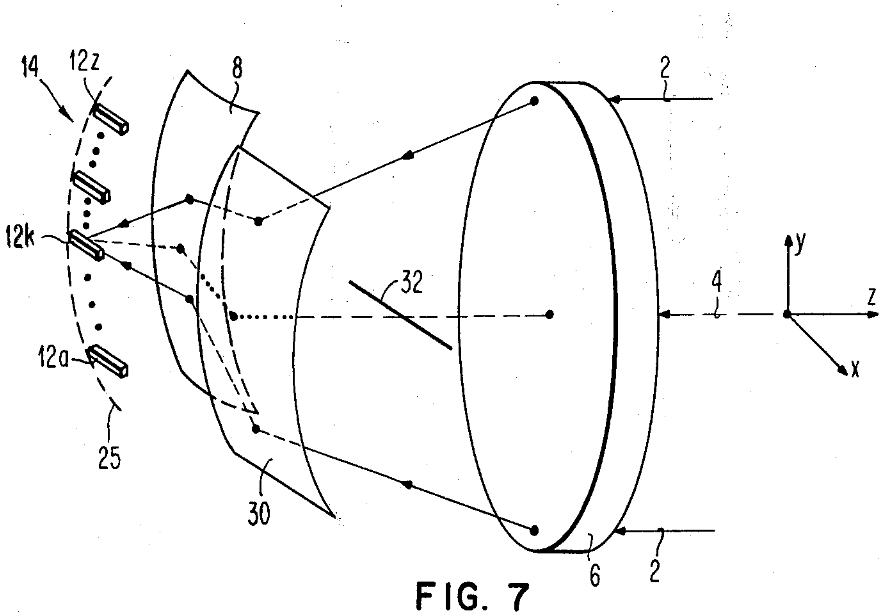
FIG. 7 is a perspective view of the receiving unit illustrated in FIG. 6.

In FIGS. 1–5 a first embodiment of an ultrasonic apparatus according to the invention is illustrated, and in FIGS. 6 and 7 a second embodiment of an ultrasonic apparatus according to the invention is shown. In order to facilitate the consideration of the drawings, a system of three orthogonal coordinates x, y, z has been introduced in all FIGS. 1–7.

Figure 1:
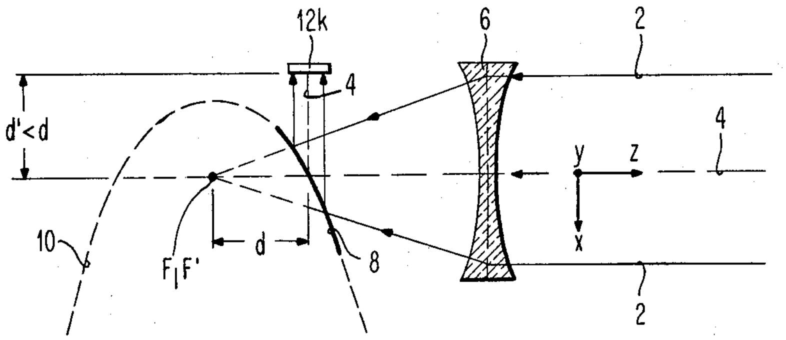
FIG. 1 is a cross-sectional view of the receiving unit of an ultrasonic apparatus according to a first embodiment of this invention wherein a parabolic cylinder mirror is used.

With referene to FIG. 1, a cross-sectional top view of the receiving unit of an ultrasonic apparatus, in particular of an ultrasonic transmission camera, is illustrated. Ultrasound beams 2 are transmitted parallel to a main imaging axis or an acoustic imaging axis 4. The imaging axis is parallel to the z-axis of the coordinate systems x, y, z. The ultrasound beams 2 impinge on an imaging or focusing lens 6. This lens 6 may also be represented by a lens system. The imaging lens 6 causes the beams 2 to bend toward a common focal point. Other ultrasound beams, whose projections on the x-z plane are parallel to beams 2 but are at an angle to beams 2 when projected onto the y-z plane, are focused by the lens 6 to points above and below the focal point F. The focal line formed by these points is perpendicular to the plane of the drawing in FIG. 1. Generally the focal line may be curved.

On their ways the converging beams 2 impinge on an acoustic mirror 8 which is located at a distance d from the focal point or line F. The acoustic mirror 8 contains a reflecting surface which has a diverging effect on impinging beams of ultrasound waves.

Figure 2:
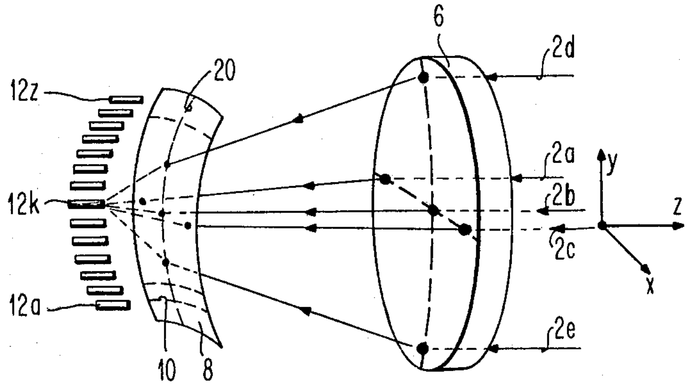
FIG. 2 is a perspective view of the receiving unit illustrated in FIG. 1.
Figure 3:
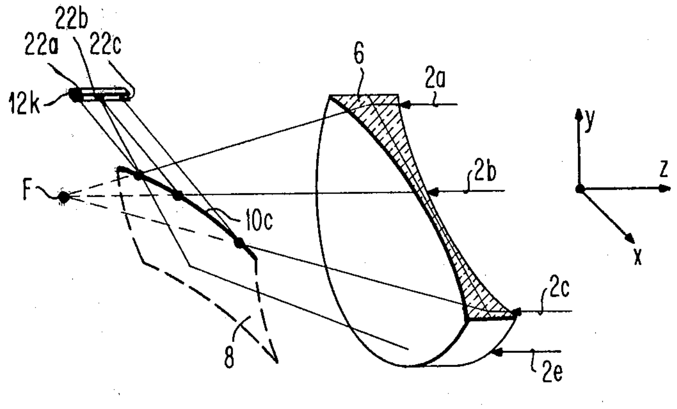
FIG. 3 is a partial view of the illustration in FIG. 2, showing a parabolic mirror and depicting its curved cross-sectional middle line.

As illustrated in FIG. 2, the acoustic mirror 8 is a portion of a curved parabolic cylinder. This cylinder can be thought of as being formed by a large number of parallel parabolic lines. Below, these parabolic lines will be referred to as "cross-sectional lines 10". Only one parabolic cross-sectional line 10 of this cylinder can be seen in FIG. 1. As a first approximation it will be assumed that the other cross-sectional lines are parallel to the line 10 and arranged one above the other such that the cylinder is a straight parabolic cylinder extending in the y-direction. The focal line F' of the parabolic cylinder coincides with the focal line F of the focusing lens 6. The main imaging axis 4 intersects the focal lines F, F'. The distance between the focal lines F, F' from the point of impingement of the center ray upon the mirror 8 is d. Further details of the acoustic mirror 8 are illustrated in FIGS. 2 and 3, although shown for a curved mirror 8 to be described below. It has just been mentioned that the cross-sectional lines 10 of the mirror 8 illustrated in FIG. 1 are parabolic. Instead of parabolic cross-sectional lines 10, there may also be used other conic sections such as elliptic or hyperbolic cross-sections, or even circular cross-sections. Such designs, however, may be more advantageously used in connection with the design shown in FIGS. 6 and 7.

The preferred arrangement shown in FIG. 1 makes sure that the converging beams 2 of the impinging ultrasound wave are reflected by the mirror 8 in parallel i.e. they are collimated. They finally arrive at an elongated piezoelectric detector element **12*k* which is part of an ultrasound detector or receiver array 14. The detector element 12*k* is positioned preferably at a location $d' < d$ although this distance d' may be extended without changing the essence of this invention. Here are focused all ultrasound beams 2 parallel to the main axis 4**.

The individual detector elements **12*a*-12*k*-12*z* are located parallel to each other in the y-z plane, that is, in a vertical plane which is perpendicular to the x-z plane of FIG. 1**.

In a first aproximation it had been assumed above that a mirror 8 is used which is a straight vertical cylindrical section of a parabolic mirror. Yet, such a mirror 8 does not have a focal line F' which extends exactly along the main imaging focal line of the imaging system which is generally curved. In order to bring the focal line F' of the mirror 8 more precisely along the curved imaging focal line F, the parabolic mirror 8 is in fact not a straight vertical mirror, but a bent or curved cylindrical section of a parabolic mirror. This is illustrated in FIGS. 2–4.

According to FIGS. 2–4, the mirror 8 is not a portion of a "straight parabolic cylinder" but a portion of what is referred to as a "bent parabolic mirror". In FIG. 4 the back side of the reflecting surface is illustrated. The individual parabolic cross sectional lines are again referred to as 10. The middle line connecting all middle points of the parabolic cross-sectional line 10 is referred to as section line 20. The section line 20 is arranged perpendicularly to all cross-sectional lines 10. In a straight vertical cylindrical section of a parabolic mirror 8, that is, in a design according to the first assumption, this section line 20 would be a straight line. In the "bent parabolic mirror" of FIG. 4, however, the section line 20 of the mirror surface (which line 20 is again arranged perpendicular to the individual cross-sectional lines 10) is bent or curved concavely with respect to the ultrasound waves arriving along the z-axis. Thus, the reflecting surface is formed like a saddle.

Even though the curvature of such a reflecting mirror 8 seems to be complex, the mirror 8 is relatively easy to manufacture. Once a mold has been made, the mirror 8 may be formed, for instance, by plastic foam. It may also be made out of glass. No matching layers are required.

If a "bent parabolic mirror" in accordance with FIG. 4 is used, the ultrasound detector 14 may preferably comprise an array 14 of individual elongated piezoelectric detector elements **12*a*–12*z*** which is shaped as illustrated in FIG. 5. According to FIG. 5, the individual detector elements 12a–12z are staggered sideways in the y-z plane along a curved path 21. The arrangement in FIG. 5 can be described in that the receiving elements 12a–12k–12z are staggered with respect to each other such that the elements on both sides adjacent to the central axis 4 are closer to the ultrasound source than the element 12k located on the central axis 4. It will be noted that also in this arrangement the longitudinal axes of the elements 12a–12z are arranged parallel to each other.

The line of bent focus or curved path 21 can be approximated by a line 21 which is an arc of a circle.

In other words, the reason for the curvature of the line 20 (see FIG. 4) and the line 21 (see FIG. 5) is the following: In the present ultrasonic apparatus the images should have a high quality. Generally, the imaging lens 6 will produce an image which does not lie on a flat plane, but rather lies on a curved surface. It is necessary, therefore, to curve the receiving array 14 such that it matches the curvature of the surface. Likewise, in order to achieve the proper collimating effect, the mirror 8 in this ultrasound apparatus must also be curved.

Now the function of the apparatus illustrated in FIGS. 1–5 will be explained in more detail. According to FIGS. 2 and 3, three beams 2a, 2b, 2c located in the x-z plane are caused to converge by the lens 6. They impinge on the central cross-sectional line 10c of the mirror 8. Subsequently, they are reflected towards the detector element 12k where they impinge on different locations 22a, 22b, 22c, respectively. Three beams 2d, 2b and 2e, which are located in the y-z plane, impinge on the mirror surface along the section line 20. Here they are reflected. They all come to focus at the point location 22b in the center of the detector element 12k. A displacement of a beam 2d, 2b, 2e out of the y-z plane will result in a displacement of the location 22b on the detector element 12k, whereas any displacement in the +y or −y direction will not cause any displacement of the location 22b of impingement on the detector element 12k.

The detector elements 12a–12z (excluding the element 12k) are needed when the beams 2a–2e are not parallel to the central axis 4, but still parallel to each other. Any angular displacement in the y-z plane will result in a displacement of the impingement location from one detector element to another.

In some instances, it may be difficult to produce the staggered array illustrated in FIG. 5. In particular, there may be little space, and the wiring may become difficult. In these cases, the ultrasonic apparatus illustrated in FIGS. 6 and 7 may be used.

This embodiment incorporates a double mirror solution. In this ultrasonic apparatus, an additional mirror 30 is positioned between the lens 6 and the parabolic mirror 8. The additional mirror 30 is a "flat mirror" which is preferably positioned at an angle of 45° with respect to the acoustic imaging axis 4. d is the distance of impingement of the central beam from the focal line F. The "flat mirror" 30 reflects the converging ultrasound beam 2 towards the mirror 8. The mirror 8 is again a section of a parabolic mirror. A parabolic cross-sectional line is again denoted as 10. The focal line F′ of the parabola coincides with the reflected image of the focal line F along which the beams 2 are focused. The distance between the location of impingement of the central beam and the focal line F′ is d′. The mirror 8 reflects the impinging beams as parallel beams towards a transducer array 14. The central element 12k of this array 14 is specifically denoted in FIGS. 6 and 7.

The detector elements 12a–12z are again straight elongated elements whichh are arranged parallel to each other. However, a staggered array of these elements 12a–12z, as shown in FIGS. 2 and 5, is no longer necessary. The elements 12a–12z are arranged along a curved line 25 of best focus. Therefore, the receiving array 14 is essentially the same design as conventionally used.

As can be seen in FIG. 7, the "flat mirror" 30 is bent concavely with respect to the arriving ultrasound waves. Preferably, the curvature of the "flat mirror" 30 is that of a portion of an elliptical cylinder. The axis 32 of symmetry of the "flat mirror" is preferably arranged at an angle of 45° between the x-axis and the z-axis. The additional miror 30 in conjunction with the bent parabolic mirror 8 serves to project the ultrasound onto a curved surface of best focus. On this curved surface of best focus, all elongated elements 12a–12z are positioned parallel to each other. They are not staggered with respect to each other in the direction of their longitudinal axes. In particular, a curved array 14 of straight elements 12a–12z as used in the prior art C-scan camera systems can be applied. Such a curved array 14 can be more easily manufactured than the staggered array 14 as illustrated in FIG. 5. All elements 12a–12z lie along the curved line 25.

From FIGS. 1–7 it will be understood that instead of the conventional bent or curved cylinder lens, an acoustic mirror 8 or mirror system is introduced by the invention. This mirror 8 has a diverging effect for ultrasound in one plane only. It yields the positive effects of such a cylinder lens without the negative effects of reverberations involving this lens. The image quality is therefore increased. In addition, less ultrasonic attenuation occurs, thereby improving the receiver sensitivity.

While the forms of the ultrasound apparatus or camera herein described constitute preferred embodiments of the invention, it is to be understood that the invention is not limited to these precise forms of assembly, and that a variety of changes may be made therein without departing from the spirit and scope of the invention.

What is claimed is:

1. An ultrasonic apparatus, comprising:

(a) focusing means for focusing ultrasound waves;

(b) an diverging acoustic mirror positioned behind said focusing means and containing a reflecting surface; and (c) an ultrasound detector containing a plurality of elongated detector elements;

wherein said reflecting surface of said diverging acoustic mirror reflects converging ultrasound waves from said focusing means such that the beams arriving so as to focus on a single point are diverged such as to focus along a focal line and wherein said ultrasound detector is positioned at said focal line for receiving said diverged ultrasound waves from said diverging acoustic mirror.

2. The improvement according to claim 1, wherein said acoustic mirror is formed by a plastic foam.

3. The improvement according to claim 1, wherein an additional mirror is interposed between said focusing means and said mirror, said additional mirror reflecting said converging ultrasound waves towards said mirror.

4. The improvement according to claim 3, wherein said focusing means is an imaging lens.

5. The improvement according to claim 3, wherein said additional mirror is curved concavely with respect to said arriving converging ultrasound waves.

6. The improvement according to claim 3, wherein said additional mirror has a cross-section which is a conic section.

7. The improvement according to claim 6, wherein said additional mirror is an ellipsoidal mirror.

8. An ultrasonic apparatus, comprising:

(a) focusing means for focusing ultrasound waves;

(b) an diverging acoustic mirror positioned behind said focusing means and containing a reflecting surface; and (c) an ultrasound detector containing a plurality of elongated detector elements;

wherein said reflecting surface of said diverging acoustic mirror reflects converging ultrasound waves from said focusing means such that the beams arriving so as to focus on a single point are diverged such as to focus along a focal line and wherein said ultrasound detector is positioned at said focal line for receiving said diverged ultrasound waves from said diverging acoustic mirror; and wherein said acoustic mirror has a reflecting surface which is formed by a parabolic cylinder.

9. The improvement according to claim 8, wherein said reflecting surface which is formed by a parabolic cylinder is curved concavely in two directions which are perpendicular to each other such that said reflecting surface is formed like a saddle.

10. The improvement according to claim 9, wherein said elongated detector elements of said ultrasound detector are staggered with respect to each other along a curved path.

* * * * *